(12) United States Patent
Sacherer

(10) Patent No.: US 8,003,052 B2
(45) Date of Patent: Aug. 23, 2011

(54) DIAGNOSTIC TAPE CASSETTE

(75) Inventor: Klaus-Dieter Sacherer, Kirchheim (DE)

(73) Assignee: Roche Diagnostics Operation, Inc., Indianapolis, IN (US)

( * ) Notice: Subject to any disclaimer, the term of this patent is extended or adjusted under 35 U.S.C. 154(b) by 1031 days.

(21) Appl. No.: 11/769,350

(22) Filed: Jun. 27, 2007

(65) Prior Publication Data
US 2008/0008989 A1   Jan. 10, 2008

(30) Foreign Application Priority Data

Jun. 27, 2006   (EP) .................................. 06013199

(51) Int. Cl.
*G01N 21/00* (2006.01)
*G01N 31/00* (2006.01)
*G01N 33/00* (2006.01)

(52) U.S. Cl. .......... 422/66; 422/112; 422/400; 422/410; 422/52; 422/63; 422/64; 422/67; 422/68.1; 422/82.03; 422/82.05; 436/2; 436/44; 436/518; 436/55; 436/164; 436/165; 204/403.03; 204/403.14; 204/415; 73/863.12; 73/864.91; 205/777.5; 210/91; 221/232; 221/270; 435/287.2; 435/7.92; 600/316; 600/347; 600/365; 600/583; 600/584; 606/181; 62/271; 5/600

(58) Field of Classification Search ............... 422/50, 422/58, 61, 63, 66, 102, 112, 400, 410, 52, 422/64, 67, 68.1, 82.03, 82.05; 436/44, 2, 436/518, 55, 164, 165; 204/403.03, 403.14; 204/415; 73/863.12, 864.91; 205/777.5; 210/91; 221/232, 270; 435/287.2, 7.92; 600/316, 347, 365, 583, 584; 606/181; 62/271; 5/600

See application file for complete search history.

(56) References Cited

U.S. PATENT DOCUMENTS

| | | | | |
|---|---|---|---|---|
| 3,607,099 A | * | 9/1971 | Scordato et al. | 422/64 |
| 3,728,081 A | * | 4/1973 | Bidanset | 422/66 |
| 4,158,450 A | * | 6/1979 | Suzuki | 248/694 |
| 4,218,421 A | | 8/1980 | Mack, Jr. et al. | |
| 4,453,189 A | * | 6/1984 | Ida | 360/96.3 |
| 4,511,941 A | * | 4/1985 | Ida | 360/251 |
| 4,573,011 A | * | 2/1986 | Rochat et al. | 324/750.04 |

(Continued)

FOREIGN PATENT DOCUMENTS

DE    4339450 A1    5/1995

(Continued)

OTHER PUBLICATIONS

Haack, U; "Outsert-Technik, Verfahren zur Wirtschaftlichen Herstellung Feinwerktechnischer Bauteile;" F&M Feinwerktechnik & Messtechnik; 449 Feinwerktechnik & Messtechnik, vol. 87 No. 6; Sep. 1979; pp. 253-259; XP001173671; ISSN: 0340-1952; Hanser, Munchen, DE.

Primary Examiner — In Suk Bullock
Assistant Examiner — Dennis M White
(74) Attorney, Agent, or Firm — Baker & Daniels LLP

(57) ABSTRACT

A diagnostic tape cassette especially for blood sugar tests comprises a test tape which is provided with a plurality of test fields for analysing body fluid, and a housing for receiving the test tape. The housing may have at least one housing part formed from a metal support and moulded-on plastic with integrated functional elements.

41 Claims, 1 Drawing Sheet

U.S. PATENT DOCUMENTS

| | | | | |
|---|---|---|---|---|
| 4,926,278 A * | 5/1990 | Schoenmakers | | 360/130.21 |
| 4,955,934 A * | 9/1990 | Stehr | | 73/862.326 |
| 5,122,969 A * | 6/1992 | Seshimoto et al. | | 702/19 |
| 5,148,350 A * | 9/1992 | Chan et al. | | 361/721 |
| 5,232,668 A * | 8/1993 | Grant et al. | | 422/82.05 |
| 5,354,531 A * | 10/1994 | Gumbert | | 264/242 |
| 5,479,305 A | 12/1995 | Kammler et al. | | |
| 5,541,809 A * | 7/1996 | Kakizaki et al. | | 361/679.33 |
| 5,575,433 A * | 11/1996 | Kammler et al. | | 242/358 |
| 5,579,187 A * | 11/1996 | Kawaguchi et al. | | 360/85 |
| 5,679,311 A * | 10/1997 | Harttig et al. | | 422/547 |
| 5,782,422 A * | 7/1998 | Fukuda et al. | | 242/347 |
| 5,993,718 A | 11/1999 | Gumbert | | |
| 6,151,110 A * | 11/2000 | Markart | | 356/244 |
| 6,534,017 B1 * | 3/2003 | Bottwein et al. | | 422/561 |
| 6,988,996 B2 * | 1/2006 | Roe et al. | | 600/584 |
| 7,169,355 B1 * | 1/2007 | Shin et al. | | 422/63 |
| 7,225,521 B2 * | 6/2007 | Krause et al. | | 29/469.5 |
| 7,455,451 B2 * | 11/2008 | Pearl et al. | | 374/141 |
| 7,638,095 B2 * | 12/2009 | Sabol | | 422/68.1 |
| 7,758,808 B2 * | 7/2010 | Harttig et al. | | 422/420 |
| 2002/0120216 A1 * | 8/2002 | Fritz et al. | | 600/583 |
| 2002/0188224 A1 * | 12/2002 | Roe et al. | | 600/584 |
| 2003/0044318 A1 * | 3/2003 | Olson | | 422/58 |
| 2003/0085124 A1 * | 5/2003 | Ufer | | 204/400 |
| 2003/0211619 A1 * | 11/2003 | Olson et al. | | 436/44 |
| 2004/0120861 A1 * | 6/2004 | Petroff | | 422/100 |
| 2005/0245845 A1 * | 11/2005 | Roe et al. | | 600/583 |
| 2006/0032745 A1 * | 2/2006 | Davies et al. | | 204/431 |
| 2006/0079811 A1 * | 4/2006 | Roe et al. | | 600/583 |
| 2006/0173380 A1 * | 8/2006 | Hoenes et al. | | 600/583 |
| 2006/0233663 A1 * | 10/2006 | Harttig et al. | | 422/58 |
| 2006/0240403 A1 * | 10/2006 | List et al. | | 435/4 |
| 2007/0100365 A1 | 5/2007 | Deck | | |
| 2007/0173740 A1 * | 7/2007 | Chan et al. | | 600/583 |
| 2008/0008989 A1 * | 1/2008 | Sacherer | | 435/4 |
| 2008/0199364 A1 * | 8/2008 | Charlton | | 422/102 |
| 2009/0098644 A1 * | 4/2009 | Sacherer et al. | | 435/287.7 |
| 2009/0200413 A1 * | 8/2009 | Sacherer | | 242/538 |
| 2009/0275861 A1 * | 11/2009 | Ruhl et al. | | 600/583 |
| 2010/0198109 A1 * | 8/2010 | Harttig | | 600/583 |

FOREIGN PATENT DOCUMENTS

| | | |
|---|---|---|
| DE | 102004024970 A1 | 12/2005 |
| EP | 0595407 B1 | 5/1997 |
| WO | WO2004/056269 A1 | 7/2004 |

* cited by examiner

DIAGNOSTIC TAPE CASSETTE

BACKGROUND OF THE INVENTION

1. Field of the Invention

The invention concerns a diagnostic tape cassette especially for blood sugar tests. The invention also concerns a production process for such a tape cassette.

2. Description of the Prior Art

Individual test strips have been used up to now in practice for the self-diagnosis of diabetics which are analysed photometrically or electrochemically after applying a small quantity of sample in order to determine the glucose content in the sample (blood or tissue fluid) as exactly and reliably as possible. In order to improve the user friendliness, it has already been proposed that a plurality of tests be provided on a test tape in the form of a tape cassette. It should be possible to use such tape cassettes as a disposable part in compact hand-held devices in order to be able to carry out all necessary analytical steps automatically and rapidly. In this connection it should be noted that the consumable parts are a mass-produced article on which high demands are made due to the required reliability.

SUMMARY OF THE INVENTION

It is proposed according to the invention that the housing has an outsert moulding part formed by outsert technology from a metal support and moulded-on plastic. The outsert moulding technique may allow for the cost-effective manufacture of metal-plastic composite parts in which material bridges and undercuts ensure a rigid connection. With regard to a diagnostic tape cassette, this allows functional elements for special purposes to be integrated into the housing and also into the metal support without having to manufacture and manipulate separate components. In particular the metal support prevents changes in shape that can occur when only plastic parts are used even during long-term storage or long-term use in an instrument, wherein a high housing strength can be achieved even with small wall thicknesses. This may allow for compact designs with a high storage density of the tests to be manufactured.

The functional elements integrated into the outsert moulding part comprise spring, connecting and/or guide elements for a particularly practical cassette arrangement.

The functional elements may comprise at least one spring element formed on the metal support. This spring element does not then have to be separately inserted into the housing but rather can be integrated into the outsert moulding part in the desired position in one operation.

Another embodiment provides that the metal support is preformed from precut metal sheet thus allowing thin but nevertheless stable housing walls to be realized.

A precut part of the metal sheet blank is bent as an elastically resettable spring element. In certain embodiments, a functional element is provided in the form of a leaf spring for a sealing function with respect to the test tape.

Another simplification provides that a free end of the leaf spring is detachably held in a pretensioned position by a wall made of moulded-on plastic and, where appropriate, is only brought into the designated operating position during the final assembly.

A functional element in the form of a spiral spring may be present to spring-load a tape reel. In this ease the spiral spring may be recessed relative to a plane of the metal support and may be bent out into the interior of the housing in a coil shape. This configuration also protects the inner space of the housing from contamination by covering the spiral spring against contact from outside with a cover made of moulded-on plastic.

In order to be able to manipulate the spring function and positioning, the moulded-on plastic may include at least one cut-out in the wall for a pusher and/or centering pin.

Another embodiment provides that the functional elements comprise at least one anchoring element for the outsert moulding part. This can be achieved by coating supporting hooks that protrude from the metal support with plastic in the form of a snap-in element.

Another housing function may be achieved by means of the fact that the functional elements comprise a cover for the test tape transported between the tape reels. The cover can be formed by undercut flaps of the metal support that are coated with plastic.

In order to ensure the tape runs with the lowest possible frictional losses, the functional elements may comprise a tape deflector as a guide slide bearing for the test tape.

The outsert moulding part forms a housing part and in particular a cassette cover or a cassette body for the tape cassette.

The process of forming embodiments of the invention may be achieved by preforming a metal support preferably as a metal sheet blank and providing it with moulded-on plastic parts by injection moulding in the outsert technique during which functional elements for the tape cassette are integrated into the outsert moulding part that is formed in this manner.

BRIEF DESCRIPTION OF THE DRAWINGS

The invention is further elucidated in the following on the basis of the embodiment example shown schematically in the drawing.

DETAILED DESCRIPTION OF EMBODIMENTS OF THE INVENTION

Figure 1:
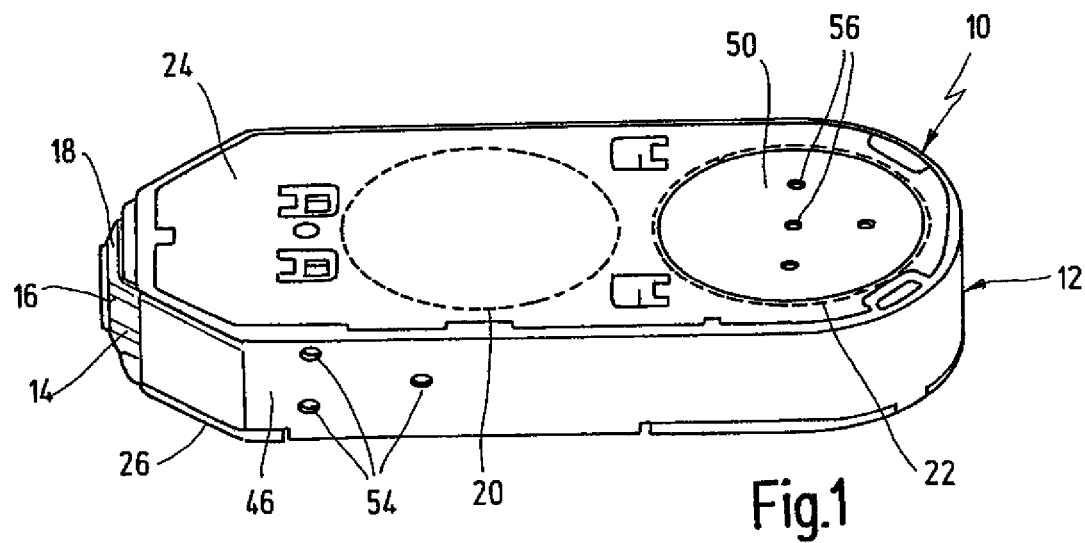
FIG. 1 shows a tape cassette for blood sugar tests in a perspective view.

The tape cassette 10 shown in the drawing enables a plurality of glucose analyses to be carried out locally on blood samples that are collected by the patient himself. For this purpose a housing 12 is designed to receive a test tape 14 which is provided with a plurality of test fields 16 to which blood can be successively applied at an application point 18. The tape is transported by means of two tape reels 20, 22 inserted into the housing 12. The basic sequence of the analysis is derived for example from WO 2004/056269 which is hereby expressly incorporated by reference herein.

Figure 2:
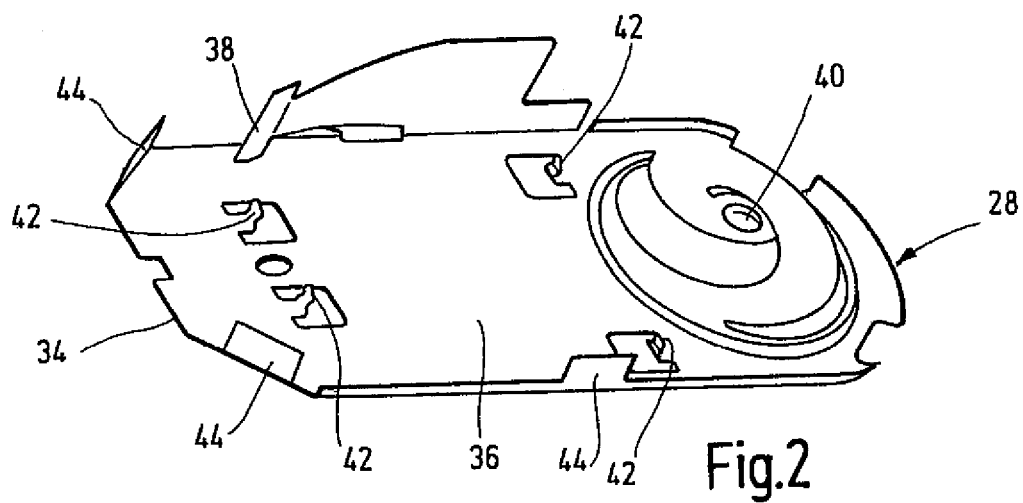
FIG. 2 shows a metal support for a cover part of the tape cassette in a perspective inner view.

The housing 12 comprises an outsert moulding part 24 designed as a cover part cassette body 26 that can be connected thereto. The outsert moulding part 24 is formed using the outsert technique from a metal support 28 an embodiment of which is shown in FIG. 2 and plastic 30 that is moulded thereon. In this manner it is possible to integrate various functional parts 32 onto the prefabricated part. In the outsert technique, the metal support 28 is placed in the hollow tool space of a closable moulding tool and enclosed by a hardenable plastic mass by means of injection moulding. In this process the plastic may be rigidly anchored to the metal support by undercuts and cut outs. The process as such is known to a person skilled in the art so that it is not necessary to describe further details of the process here.

FIG. 2 shows the metal support 28 that has been shaped as a precut metal sheet 34 by punching and bending. The pre-cut part 34 has a flat base area 36 from which various functional parts, in particular spring elements 38, 40 and supporting elements 42, 44 are bent out.

A leaf spring 38 is provided at a bevelled side face to improve the sealing function against the test tape 14 which is guided over a seal that is not shown. In order to apply a spring force to the tape spool 22, a spiral spring 40 is located in the base area region 36 where the moulded-on end of the spring 40 is deep-drawn in a circular shape, and the free end of the spring is bent out in a spiral shape towards the inside of the housing.

Several angled, laterally undercut supporting hooks 42 are distributed on the base area 36 to stabilize the moulded-on anchoring elements. Flaps 44 are provided as lateral supporting elements on the edge side of the base area 36.

Figure 3:
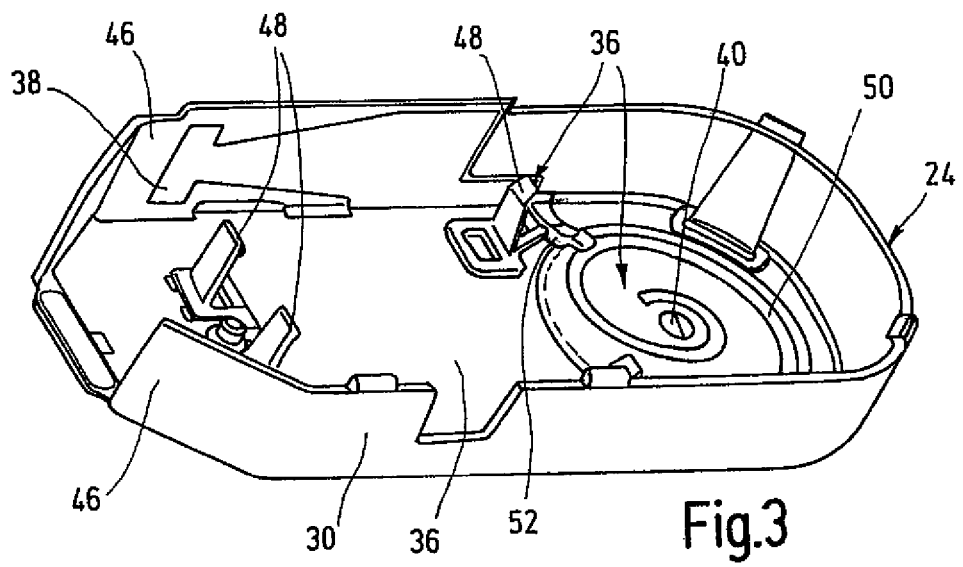
FIG. 3 shows a cover part formed using outsert technique in a view according to FIG. 2.

With reference again to FIG. 1 through FIG. 3, the finished outsert moulding part 24 has side walls 46 supported by the flaps 44 which cover the test tape 14 towards the outside with the exception of the area of the application tip 18. Locking hooks 48 may be made of plastic and are moulded-on to the supporting hooks 42 for a snap lock with the cassette body 26. The spiral spring 40 is protected against contact from outside by a cap 50 made of plastic in the plane of the base area 36. The cap 50 may be permanently connected to the metal support 28 by means of an opposing moulded point 52 on the inside of the base area 36.

In the injection moulding tool, the leaf spring 38 is pretensioned in the region of the adjoining sidewall 46 and is fixed there by centering pins (not shown) until the solidified plastic adopts its holding function due to its shrinking property. The centering pins form wall openings 54 in the plastic on the outside of the cap member 24, as depicted in FIG. 1. During final assembly, the spring 38 can be pressed out towards the inside into its active position by means of a pusher (not shown) which engages through the openings 54. Corresponding openings 56 are also present in the area of the cover 50 of the spiral spring 40.

It is also basically possible that other parts of the cassette 10 may be formed using the outsert technology. In particular the cassette body 26 can have a metal support on which tape deflectors for the test tape 14 are moulded. These can be kept free towards the outside after moulding-on the parts of the body that are formed from plastic such that the test tape 14 which is guided between the reels 20, 22 over the tip 18 glides on the metallic tape deflectors (not shown).

While the invention has been taught with specific reference to these embodiments, one skilled in the art will recognize that changes can be made in form and detail without departing from the spirit and scope of the invention. The described embodiments are to be considered, therefore, in all respects only as illustrative and not restrictive. As such, the scope of the invention is indicated by the following claims rather than by the description.

The invention claimed is:

1. A diagnostic tape cassette including:
   a test tape including a plurality of test fields comprising a test reagent for diagnostic testing of a body fluid; and
   a housing comprising a base portion and a cap member, the cap member having a plurality of sides and configured to receive at least a portion of the test tape and couplable to the base portion, the cap member including a metal support and plastic moulded onto at least a portion of the metal support, wherein the plastic is moulded onto the metal support by way of outsert moulding, and at least one of the plurality of sides comprises a portion of the metal support and plastic moulded onto the metal support.

2. The diagnostic tape cassette as set forth in claim 1 wherein the cap member includes at least one integrated functional element.

3. The diagnostic tape cassette as set forth in claim 2 wherein the functional element includes at least one spring element.

4. The diagnostic tape cassette as set forth in claim 2 wherein the functional element includes a leaf spring.

5. The diagnostic tape cassette as set forth in claim 4 wherein the leaf spring includes a free end retained in a first position by a wall, wherein the wall comprises a portion of at least one of the plurality of sides of the cap member formed of plastic moulded onto the metal support by way of outsert moulding.

6. The diagnostic tape cassette as set forth claim 2 wherein the functional element includes a spiral spring configured to spring-load a tape reel.

7. The diagnostic tape cassette as set forth in claim 6 wherein the spiral spring is at least partially located in a recess formed in the metal support and a portion of the spiral spring extends at least partially into the interior of the cap member.

8. The diagnostic tape cassette as set forth in claim 7 wherein at least a portion of the spiral spring is covered by a cover formed of plastic.

9. The diagnostic tape cassette as set forth in claim 3 wherein the plastic moulded onto the metal support defines at least one opening configured to receive a member capable of acting on the spring element.

10. The diagnostic tape cassette as set forth in claim 2 wherein the functional element includes at least one anchoring element.

11. The diagnostic tape cassette as set forth in claim 2 wherein the functional elements include a cover configured to cover at least a portion of the test tape.

12. The diagnostic tape cassette as set forth claim 11 wherein the cover includes a plurality of undercut flaps formed in the metal support and the undercut flaps are at least partially coated with plastic.

13. The diagnostic tape cassette as set forth in claim 2 wherein the functional element further includes a tape deflector that provides a bearing surface for the test tape.

14. The diagnostic tape cassette as set forth in claim 1 wherein the metal support is formed from a pre-cut metal blank.

15. The diagnostic tape cassette as set forth in claim 14 wherein the pre-cut metal blank includes a bend portion forming a spring.

16. The diagnostic tape cassette as set forth in claim 1 further including at least one support hook protruding from the metal support and coated with plastic.

17. A method of manufacturing a tape cassette for diagnostic testing, the method including the steps of:
   providing a metal blank,
   bending at least one portion of the metal blank;
   moulding plastic onto the metal blank such that a cap member having a plurality of sides is formed, at least one of the plurality of sides comprising the moulded plastic;
   providing a test tape having a plurality of testing fields comprising a test reagent for diagnostic testing of a body fluid;
   providing a base portion adapted to support the test tape and supporting the test tape with the base portion; and coupling the cap member to the base portion such that at least a portion of the test tape is located in the cap member, wherein the step of coupling is reversible.

18. The method as set forth in claim 17 wherein the step of moulding plastic onto the metal support comprises an outsert moulding process.

19. The method as set forth in claim 18 further including the step of forming a spring in the metal blank.

20. The method as set forth in claim 19 wherein the spring includes a spiral spring.

21. The method as set forth in claim 19 wherein the spring includes a leaf spring.

22. The method as set forth in claim 21 wherein a portion of the plastic biases at least a portion of the leaf spring.

23. The method as set forth in claim 19 further including the step of forming a plurality of openings in the moulded plastic configured to allow a member to act on the spring.

24. The method as set forth in claim 17 further including the steps of:
forming a plurality of undercut flaps in the metal blank; and
moulding plastic over the undercut flaps.

25. The method as set forth in claim 17 further including the steps of:
forming a plurality of support hooks in the metal blank; and
moulding plastic over the support hooks, wherein the step of moulding plastic over the support hooks forms a plurality of plastic overmoulds.

26. A diagnostic tape cassette for performing blood glucose tests including:
a test tape including a plurality of test fields comprising a test reagent for blood glucose testing of a body fluid; and
a housing comprising a cap member and a base member, wherein the cap member includes a metal support with a plastic overmould thereon is formed by an outsert moulding process, the base member adapted to support the testing tape, and the cap member configured to couple to the base member such that the cap member receives at least a portion of the test tape.

27. The diagnostic tape cassette as set forth in claim 26 wherein the metal support includes a leaf spring and a spiral spring.

28. The diagnostic tape cassette as set forth in claim 27 wherein the plastic overmould defines at least one opening configured to allow a member to act on the leaf spring.

29. The diagnostic tape cassette as set forth in claim 28 wherein the plastic overmould includes a wall configured to bias the leaf spring into a pre-loaded position.

30. The diagnostic tape cassette as set forth in claim 26 further including a plurality of support hooks formed in the metal support and coated with plastic.

31. The diagnostic tape cassette as set forth in claim 26 wherein the metal support includes a plurality of undercut flaps coated with plastic.

32. The diagnostic tape cassette of claim 1, wherein the plastic moulded onto the metal support comprising the side is integral with plastic moulded onto another portion of the metal support.

33. The diagnostic tape cassette as set forth in claim 1, wherein the metal support comprises a single continuous piece of metal.

34. The diagnostic tape cassette of claim 10, wherein the anchoring element reversible couples the cap member to the base portion.

35. The method of claim 17, wherein the at least one side comprising the moulded plastic further comprises at least a portion of the bent portion of the metal blank.

36. The method of claim 17, wherein the moulded plastic of the cap member defines an application spot.

37. The method of claim 17, wherein the moulded plastic is an integrated single component.

38. The method of claim 25, wherein the step of coupling the cap member to the base portion utilizes the plurality of plastic overmoulds formed in the step of moulding plastic over the support hooks.

39. The diagnostic tape cassette of claim 1, wherein the body fluid is blood.

40. The method of claim 17, wherein the body fluid is blood.

41. The diagnostic tape cassette as set forth in claim 26 wherein the body fluid is blood.

* * * * *